(12) United States Patent
Feron et al.

(10) Patent No.: US 11,998,579 B2
(45) Date of Patent: *Jun. 4, 2024

(54) IMMUNOGENIC COMPOSITION

(71) Applicant: GLAXOSMITHKLINE BIOLOGICALS SA, Rixensart (BE)

(72) Inventors: Christiane Marie-Paule Simone Jeanne Feron, Rixensart (BE); Sandra Giannini, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 800 days.

This patent is subject to a terminal disclaimer.

(21) Appl. No.: 16/064,017

(22) PCT Filed: Jan. 3, 2017

(86) PCT No.: PCT/EP2017/050095
§ 371 (c)(1),
(2) Date: Jun. 20, 2018

(87) PCT Pub. No.: WO2017/114979
PCT Pub. Date: Jul. 6, 2017

(65) Prior Publication Data
US 2019/0083552 A1 Mar. 21, 2019

(30) Foreign Application Priority Data
Jan. 3, 2016 (GB) .................................. 1600075

(51) Int. Cl.
| | | |
|---|---|---|
| C12Q 1/04 | (2006.01) | |
| A61K 35/76 | (2015.01) | |
| A61K 39/00 | (2006.01) | |
| A61K 39/02 | (2006.01) | |
| A61K 48/00 | (2006.01) | |
| A61P 31/04 | (2006.01) | |
| C12N 9/24 | (2006.01) | |
| C12N 15/85 | (2006.01) | |
| C12N 15/86 | (2006.01) | |
| C40B 40/02 | (2006.01) | |

(52) U.S. Cl.
CPC .............. *A61K 35/76* (2013.01); *A61K 39/00* (2013.01); *A61K 39/02* (2013.01); *A61K 48/0008* (2013.01); *A61K 48/005* (2013.01); *A61P 31/04* (2018.01); *C12N 9/2405* (2013.01); *C12N 15/85* (2013.01); *C12N 15/86* (2013.01); *C12Y 302/01087* (2013.01); *A61K 2039/5256* (2013.01); *C12N 2795/00032* (2013.01); *C12N 2795/00034* (2013.01); *C12N 2795/00043* (2013.01); *C12N 2800/24* (2013.01); *C12N 2830/00* (2013.01); *C40B 40/02* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 6,929,798 | B2 * | 8/2005 | Pillich ..................... | A61P 17/02 |
| | | | | 424/243.1 |
| 2011/0002889 | A1 * | 1/2011 | Barrangou ........... | A23C 9/1238 |
| | | | | 424/93.2 |
| 2012/0301433 | A1 * | 11/2012 | Lu ........................... | A61P 25/28 |
| | | | | 424/93.2 |
| 2015/0047050 | A1 | 1/2015 | Kuan-Ta | |

FOREIGN PATENT DOCUMENTS

| | | |
|---|---|---|
| JP | 2014-221038 A | 11/2014 |
| WO | 2003/026691 A2 | 4/2003 |
| WO | 2003/026767 A2 | 4/2003 |
| WO | 2003/067991 A1 | 8/2003 |
| WO | 2003/076583 A2 | 9/2003 |
| WO | WO 03/076583 * | 9/2003 |
| WO | 2004/113375 A2 | 12/2004 |
| WO | WO 2011014693 * | 2/2011 |
| WO | WO 2014/085297 A1 | 8/2014 |
| WO | WO 2014/184528 A1 | 11/2014 |
| WO | 2015/116531 A1 | 8/2015 |
| WO | WO 2010/141135 A2 | 12/2018 |

OTHER PUBLICATIONS

Bao et al. ; Advanced Drug Delivery Reviews 145 (2019) 40-56.*
Clark et al., Bacterial viruses as human vaccines? Expert Rev. Vaccines 3(4), 463-476 (2004).*
Bacteriophage—Wikipedia pp. 1-13; downloaded Aug. 27, 2021.*
P1 phage—Wikipedia pp. 1-6 downloaded on Aug. 27, 2021.*
Periplasm—Wikipedia pp. 1-3 downloaded Jan. 11, 2022.*
Myoviridae—Wikipedia p. 1 of 6 downloaded Jan. 11, 2022.*
International Search report and Written Opinion issued in Application No. PCT/EP2017/050095, dated Mar. 21, 2017.
Casjens et al., "Bacteriophage lambda: Early pioneer and still relevant." Virology, vol. 479-480, 2015, pp. 310-330.
David Bikard, et al.: "Exploiting CRISPR-Cas nucleases to produce sequence-specific antimicrobials", Nature Biotechnology, Gale Group Inc., US; vol. 32 No. 11, Nov. 1, 2014, pp. 1146-1150; XP002742966.
Zhu, Daoyin, Chongqing University Press, "Immunology and Pathogenic Biology", Jan. 31, 1997, p. 67.

(Continued)

*Primary Examiner* — Maria G Leavitt

(74) *Attorney, Agent, or Firm* — Birch, Stewart, Kolasch & Birch, LLP

(57) ABSTRACT

The present invention discloses a recombinant bacteriophage comprising a phage genome polynucleotide including a gene encoding a heterologous antigen protein(s) and a killing gene encoding a protein that is capable of killing a host bacterium. Such a recombinant bacteriophage is designed to prime a subject's immune response and to kill the bacterium that it infects such that the "prime and kill" bacteriophage provides two lines of protection against infectious disease.

6 Claims, 3 Drawing Sheets

(56) References Cited

OTHER PUBLICATIONS

Wu, Deqin, "Expression of tail fiber protein gp37 of polyvalent phage Bp7 and the function in the phage reproduction", Acta Veterinaria et Zootechnical Sinica, Dec. 31, 2012, vol. 43, No. 2, pp. 324-328 (Abstract).

Wang, Fangzheng, "Lytic effect of bacteriophage and its endolysin to bovine mastitis pathogens", Progress in veterinary medicine, vol. 36, No. 4., Dec. 31, 2015, p. 113. (Abstract).

* cited by examiner

Minimum synthetic phage genome: incapable of lysogeny or propagation, only genome amplification

Expression of bio-film destroying enzyme.

Modified tail fibers/plate: broaden strain recognition.

Engineered phage genome capable of killing bacteria

Overexpression of heterologous cargo (ie antigen)

IMMUNOGENIC COMPOSITION

TECHNICAL FIELD

The present invention relates to the field of treatment or prevention of infections using recombinantly engineered bacteriophages. In particular, the present invention discloses bacteriophages which are recombinantly engineered to express antigens. Such expressed antigens can prime an immune response against an infectious agent. In addition, the recombinant bacteriophage is able to kill a host bacterium, for example, either using the bacteriophage lytic mechanism or through the expression of further antimicrobial peptides.

BACKGROUND

Bacteriophages have been known for many years having been discovered by Fredrick Twart in 1915 and Felix d'Herelle in 1917. They are viruses with DNA or RNA genomes that infect and replicate within bacteria. Bacteriophages can undergo lytic or lysogenic cycles within bacteria. During the lytic cycle, the bacteriophage genetic material is injected into a bacterium, where transcription, translation and replication take place, leading to the assembly and packaging of bacteriophage proteins and nucleic acids and eventually to lysis where many bacteriophage are released, ready to infect further bacteria. Some bacteriophages can also carry out a lysogenic cycle in which the bacteriophage genetic material is incorporated into a bacterial genome.

Bacteriophages are currently being tested in clinical studies for the treatment of bacterial infections. Pathogens such as *S. aureus, E. coli* and *P. aeruginosa* are being targeted. Wright A Clin Otolaryngol (2009) 34:349, describes a controlled clinical trail of a therapeutic bacteriophage preparation for the treatment of chronic otitis due to antibiotic-resistant *Pseudomonas aeruginosa*. Sarker S A et al. Virology (2012) 434:222 describes the administration of an oral T4-like phage cocktail to healthy adult volunteers from Bangladesh (ClinicalTrials.govidentifier: NCT01818206).

Engineered bacteriophages have been developed for multiple bacterial targets with the objective of elimination or reduction of bacterial load. Examples include; SASP gene delivery: a novel antibacterial approach. Fairhead H Drug News Perspect. (2009):197-203, Engineered Phagemids for Nonlytic, Targeted Antibacterial Therapies; Krom R J et al Nano Lett. (2015) 15, 4808-4813; Sequence-specific antimicrobials using efficiently delivered RNA-guided nucleases Citorik R J et al. Nature Biotechnology (2014) 32 1141, Exploiting CRISPR-Cas nucleases to produce sequence-specific antimicrobials, Bikard D. Nature Biotechnology (2014) 32 1146.

Moreover, engineered bacteriophage have also been developed as vaccines or for targeted delivery to kill cancer cells. However, such bacteriophages are not intended to infect bacteria (Therapeutic and prophylactic applications of bacteriophage components in modern medicine. Adhya S et al. Cold Spring Harb Perspect Med. (2014) 1 1., Killing cancer cells by targeted drug-carrying phage nanomedicines Bar H. et al. BMC Biotechnol. (2008) 37, Phage protein-targeted cancer nanomedicines Petrenko V A and Jayanna P K. FEBS Lett. (2014) 588:341).

With the growth of antibiotic resistance, it is important that further strategies are developed to treat or prevent bacterial infection. The present invention represents an advance in the use of recombinant bacteriophages. The recombinant bacteriophages of the invention not only target a bacterium for killing using the lytic machinery of the bacteriophage or other heterologous molecules to kill the bacteria, but also express an antigen. The antigen is over-expressed during the period when bacteriphage genes are transcribed and translated and is either expressed on the surface of the bacterium or released on lysis/death of the bacterium. The antigen is able to induce an immune response so that the bacteriophage is capable not only of killing the bacterium directly, but also of priming an immune response so that the bacteria can be eliminated by the immune system to eliminate residual bacteria or prevent relapse/re-infection at later time point. Hence the bacteriophage of the invention can both kill bacteria and prime the immune response to further eliminate the bacteria.

Accordingly, there is provided, a recombinant bacteriophage comprising a phage genome polynucleotide including a gene encoding a heterologous antigen protein(s) and a killing gene encoding a protein that is capable of killing a host bacterium.

In a second aspect of the invention, there is provided, a recombinant bacteriophage comprising a phage genome polynucleotide including a gene encoding a heterologous antigen protein(s), wherein the heterologous antigen protein(s) is not expressed as part of a phage coat/capsid protein, and a killing gene encoding a protein that is capable of killing a host bacterium.

In a third aspect of the invention there is provided, a recombinant bacteriophage genome polynucleotide comprising a heterologous antigen gene encoding a heterologous antigen protein, wherein the antigen gene does not encode a fusion protein of a phage capsid protein and a heterologous protein, and a killing gene encoding a protein that is capable of killing a host bacterium.

In an fourth aspect of the invention, there is provided a recombinant bacteriophage genome polynucleotide comprising a heterologous antigen gene encoding a heterologous antigen protein and a killing gene encoding a protein that is capable of killing a host bacterium.

In a fifth aspect of the invention, there is provided, a pharmaceutical composition comprising the recombinant bacteriophage or the recombinant bacteriophage genome polynucleotide of the invention.

In a sixth aspect of the invention, there is provided a vaccine comprising the recombinant bacteriophage or the recombinant bacteriophage genome polynucleotide of the invention.

In a seventh aspect of the invention, there is provided a recombinant bacteriophage comprising a phage genome polynucleotide including a gene encoding a heterologous protein, wherein the heterologous protein is not expressed as part of a phage coat/capsid protein, and a killing gene encoding a protein that is capable of killing a host bacterium for use in the prophylactic prevention of infectious disease.

In an eighth aspect of the invention, there is provided a method of treatment comprising the steps of: a) administering the recombinant bacteriophage of the invention, to a patient in need thereof such that the recombinant bacteriophage contacts a bacterium; b) entry of the phage genome polynucleotide into the bacterium, and c) expression of the heterologous antigen protein at a sufficient level for an immune response to be elicited against the heterologous protein.

DETAILED DESCRIPTION

Figure 1:
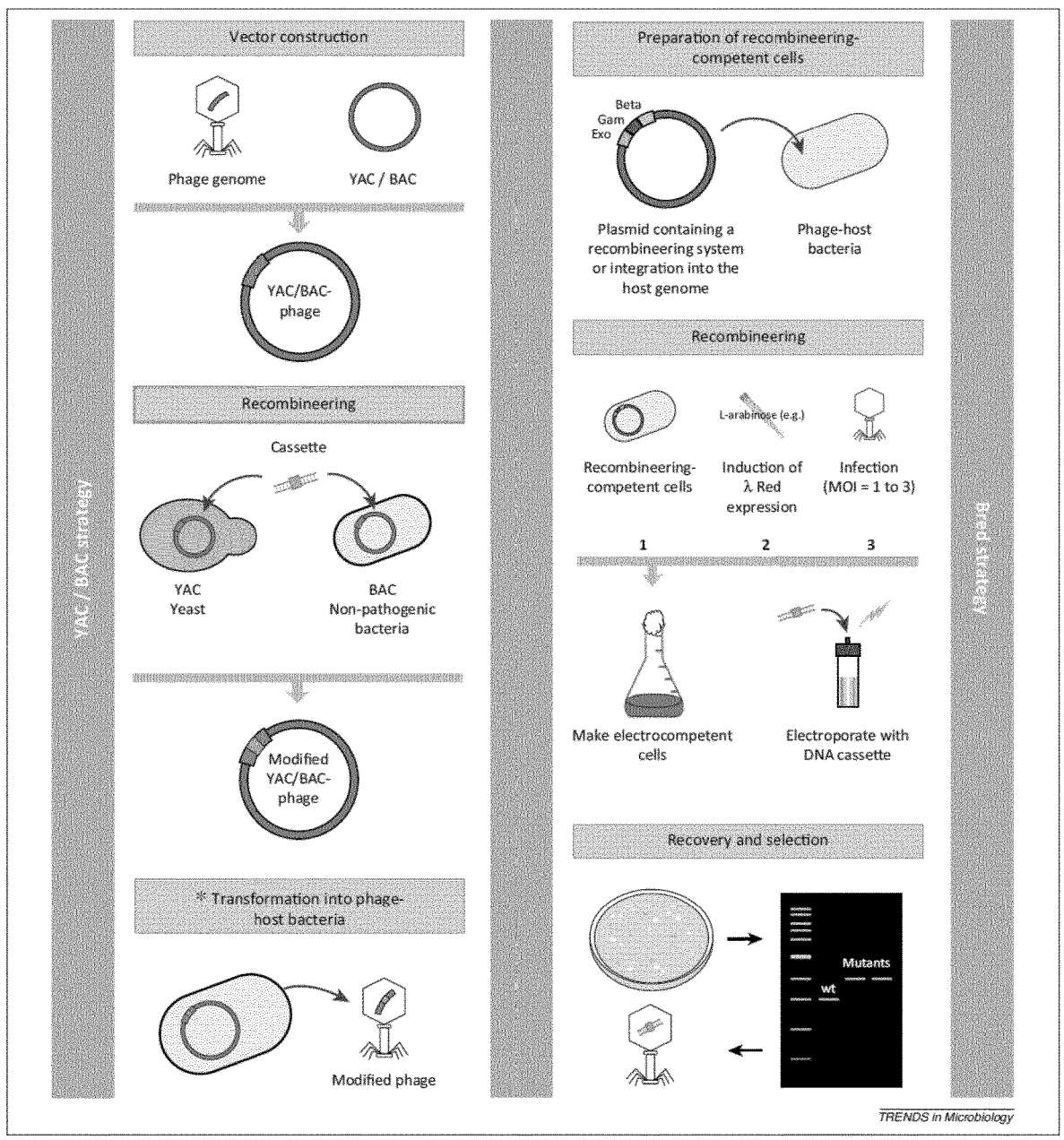
FIG. 1—demonstrates strategies for generating the recombinant bacteriophage of the invention FIG. 2—demonstrates possibilities for the genetic engineering of the recombinant bacteriophage.

The present invention discloses a recombinant bacteriophage comprising a phage genome polynucleotide including a gene encoding a heterologous antigen protein and a killing gene encoding a protein that is capable of killing a host bacterium, wherein the heterologous antigen protein is optionally not expressed as part of a phage coat/capsid protein. The recombinant bacteriophage typically comprises a viral head made up of capsid protein(s) and comprising a recombinant phage genome polynucleotide, a tail structure containing means to bind to a bacterial host cell and means to insert the recombinant phage genome polynucleotide into a host cell. The genome polynucleotide is engineered to retain sequences essential for transcription and translation of the bacteriophage genome, as well as at least the packaging signal, however other parts of the bateriophage genome may be replaced with one or more genes encoding a heterologous antigen. It is preferred that the bacteriophage genome does not contain genes encoding proteins which allow the lysogenic cycle to proceed. It is also preferred that the bacteriophage genome of the invention does not contain all the genes that allow replication and release of viable bacteriophage. Therefore genes that encode proteins involved with the initiation of the lysogenic cycle or that encode some of the structural proteins of the bacteriophage may be deleted and/or may be replaced with genes encoding at least one antigen. Optionally, the recombinant bacteriophage comprises a receptor for a host bacterium. This is typically a protein from the tail of the bacteriophage which binds specifically to a host bacterium, allowing the bacteriophage to bind to the host bacterium and insert genome polynucleotide into the host bacterium.

By "heterologous antigen" it is meant that the heterologous antigen is an antigen that is not present in the wild-type bacteriophage. It may be an antigen which is present in the bacteria that the bacteriophage is designed to infect or it may be an antigen from a different bacterium which the bacteriophage does not infect or it may be an antigen from a virus or from a fungus.

By "heterologous pathogen" it is meant a pathogen which is not a bacteriophage.

The term "host bacterium" refers to a bacterium which the recombinant bacteriophage binds to and it able to insert genome polynucleotide into.

In an embodiment the recombinant bacteriophage of the invention, encodes a heterologous antigen protein which is capable of generating an immune response against a bacterial host. In this embodiment, the recombinant bacteriophage targets the same species of bacteria by firstly entering and lysing the bacterium and also causing an antigen from the bacterium to be expressed and presented to a host's immune system such that the immune system targets and kills further bacteria of the same variety which were not initially infected by the bacteriophage. Thus the "kill and prime" concept which is part of the invention allows more efficient bacteriophage treatment of a targeted bacterium.

In a further embodiment, the recombinant bacteriophage of the invention encodes a heterologous antigen which is not present in the bacterial host of the recombinant bacteriophage. The heterologous antigen is optionally an antigen expressed by a different species of bacteria or is optionally an antigen expressed by a fungus or is a viral antigen. Thus the "kill and prime" concept of the invention allows one species of bacteria to be targeted by the bacteriophage to be killed and the express antigen which allow the host to raise an immune response against other species of bacteria, or viruses or fungi. This embodiment may therefore be useful in order to target a disease which is due to a mixture of bacterial pathogens or a mixture of bacterial and/or viral and/or fungal pathogens.

In an embodiment of the invention, a recombinant bacteriophage comprising a phage genome polynucleotide including a gene encoding a heterologous antigen protein(s) and a killing gene encoding a protein that is capable of killing a host bacterium. Thus the recombinant bacteriophage genome encodes proteins which are capable of priming an immune response and killing a host bacterium. The killing gene is optionally a bacteriophage gene encoding a protein that is capable of lysing a bacterium. The killing gene is optionally a heterologous gene with bacteriocidal activity. Examples of such genes are the CRISPR-Cas nucleases and SASP genes which encode peptides that bind to and inactivate bacterial DNA (WO 04/113375, WO 16/55585, WO 16/55584, WO 16/55586, WO 16/55587, Selle K. et al Trends Microbiol. 23 (2015) 225-232, Qi L et al Nat. Biotechnology 30, (2012) 1002-1006, Mali et al Science 339, (2013) 823-826, Gaj T. et al Trends Biotechnol. 31, (2013) 397-405, Wang H et al Cell 153, (2013) 910-918. Further examples of killing genes include those disclosed in Mehta et al, Biotechnology and Bioenginneering (2016) 113; 2568-2576; SASP gene delivery: a novel antibacterial approach. Fairhead H Drug News Perspect. (2009):197-203, Engineered Phagemids for Nonlytic, Targeted Antibacterial Therapies; Krom R J et al Nano Lett. (2015) 15, 4808-4813; Sequence-specific antimicrobials using efficiently delivered RNA-guided nucleases Citorik R J et al. Nature Biotechnology (2014) 32 1141, Exploiting CRISPR-Cas nucleases to produce sequence-specific antimicrobials, Bikard D. Nature Biotechnology (2014) 32 1146.

The choice of promoters to drive expression of the heterologous antigen protein is important since sufficient antigen should be produced before the host bacterium is killed. Therefore in an embodiment, the recombinant bacteriophage of the invention uses a strong promoter or an early promoter to drive expression from the gene encoding the heterologous antigen protein. Optionally, expression of the heterologous antigen protein is driven by a strong, early promoter. Alternatively, expression of the heterologous antigen protein is driven by a strong late promoter. In an embodiment, multiple copies of the gene encoding the heterologous antigen protein are present in the recombinant bacteriophage so that expression is increased. For example, 1, 2, 3, 4 or 5 copies of the gene encoding the heterologous antigen protein are present in the recombinant bacteriophage genome.

In an embodiment, the recombinant bacteriophage of the invention contains a phage genome polynucleotide which comprises a killing gene encoding a protein that is capable of killing a host bacterium. In an embodiment the killing gene is under the control of a late or a weak promoter. This has the advantage of ensuring that the host bacterium expresses sufficient antigen to prime an immune response before it is killed. In an embodiment, the killing gene is under the control of a promoter which is a late promoter and a weak promoter. In an embodiment, the heterologous antigen protein is driven by a strong and/or early promoter and the killing gene is under the control of a late and weak promoter.

In an embodiment, the recombinant bacteriophage is selected from the group of families consisting of; myoviridae, siphoviridae, podoviridae, corticiviridae, tectiviridae, leviviridae, cystoviridae, inoviridae, lipothrixviridae, rudiviridae, plasmaviridae and fuselloviridae. In an embodiment the bacteriophage is a myoviridae or a siphoviridae. In an embodiment, the bacteriophage is a siphoviridae.

In an embodiment, the heterologous antigen protein is a bacterial protein originating from a Gram positive or Gram negative bacterium. Optionally, the heterologous antigen protein is naturally present in a bacterium that is infectable by the recombinant bacteriophage (i.e. the host bacterium). The heterologous protein is optionally expressed at a higher level after infection with the recombinant bacteriophage. In this way an immune response can be primed against a protein in the bacterial host such that priming and killing target the same bacterium. This approach may be applicable where the heterologous antigen protein is usually expressed at a low level within the host bacterium.

In an embodiment, the heterologous antigen protein is a variant of a protein naturally present in a bacterium that is infectable by the recombinant bacteriophage (i.e. the host bacterium), wherein said variant has different antigenic or immunogenic characteristics to the wild-type of said variant. In this way an immune response can be primed against a protein in the bacterial host, such that priming and killing target the same bacterium. This approach may be applicable where the heterologous antigen protein exists in multiple serotypes and it is advantageous for an immune response to be targeted against multiple serotypes.

In an embodiment, the heterologous antigen protein is not naturally expressed in a bacterium that is infectable by the recombinant bacteriophage. In this embodiment, an immune response is primed against a different organism to the host bacterium. This allows the prime and kill concept to kill one bacterium and prime an immune response against a different organism which could be a different bacterium, a virus or a fungus. In an embodiment the heterologous antigen protein is capable of killing the host bacterium.

In an embodiment, the heterologous antigen protein is a viral protein.

In an embodiment, the heterologous antigen protein is a fungal protein. For example, a protein from *Candida albicans*.

In an embodiment, the heterologous antigen protein is a staphylococcal, streptococcal, *Shigella, Pseudomonas, Propionibacterium, Acinetobacter* or meningococcal protein or a protein from *E. Coli, P. aeruginosa, C. difficile, P. acnes, K. pneumoniae, N. gonorrhaea*.

In an embodiment, the heterologous antigen protein, after expression, is directed to the surface of a bacterium infected by the bacteriophage. This may be achieved by attaching an appropriate signal sequence to the heterologous antigen protein, for example a type I, II III or IV leader sequence. In an embodiment, the heterologous antigen protein is directed to the periplasm. This is achieved by attaching an appropriate leader sequence to the heterologous antigen protein; which is capable of directing the heterologous antigen protein to the periplasm of the bacterium acts as host to the recombinant bacteriophage.

In an embodiment, the heterologous antigen protein, after expression is released into the cytoplasm of a bacterium infected by the bacteriophage. This may be achieved by the absence of an appropriate leader sequence from the heterologous protein antigen. The heterologous antigen protein is expressed in the host bacterium and is initially present in the cytoplasm. As the host bacterium is lysed, the heterologous antigen protein is released from the bacterium and is able to interact with the immune system so that an immune response is elicited against the heterologous antigen protein. This may occur on death of the bacterium.

In an embodiment, the recombinant bacteriophage of the invention comprises a phage genome polynucleotide including at least 1, 2, 3, 4, 5, 6, 7, 8, 9 or 10 genes encoding at least 1, 2, 3, 4, 5, 6, 7, 8, 9 or 10 heterologous antigen proteins. In an embodiment each of the genes encodes a different heterologous antigen protein. In an embodiment, the genes encode multiple copies of the same heterologous antigen protein. For example 1, 2, 3, 4 or 5 genes encode copies of the same heterologous antigen protein. Alternatively 2 genes encode 2 different heterologous antigen proteins, 3 genes encode 3 different heterologous antigen proteins, 4 genes encode 4 different heterologous antigen proteins, 5 genes encod 5 different heterologous antigen proteins etc.

In an embodiment, multiple proteins from the same organism are encoded by the phage genome polynucleotide. In an embodiment, each heterologous antigen protein is from a separate organism so that an immune response against multiple organisms (1, 2, 3, 4, 5, 6, 7, 8, 9 or 10 bacterial species or a mixture of bacterial, viral and/or fungal species) is elicited. In an embodiment, the recombinant bacteriophage comprises a genome encoding at least 1 heterologous antigen protein, normally found in a single organism. In an embodiment, the recombinant bacteriophage comprises a genome encoding at least 2 heterologous antigen proteins, normally found in a single organism. In an embodiment, the recombinant bacteriophage comprises a genome encoding at least 3 heterologous antigen proteins, normally found in a single organism. In an embodiment, the recombinant bacteriophage comprises a genome encoding at least 4 heterologous antigen proteins, normally found in a single organism. In an embodiment, the recombinant bacteriophage comprises a genome encoding at least 5 heterologous antigen proteins, normally found in a single organism. In an embodiment, the recombinant bacteriophage comprises a genome encoding at least 2 heterologous antigen proteins, normally found in a two different organisms. In an embodiment, the recombinant bacteriophage comprises a genome encoding at least 3 heterologous antigen proteins, normally found in a two different organisms. In an embodiment, the recombinant bacteriophage comprises a genome encoding at least 4 heterologous antigen proteins, normally found in two different organisms. In an embodiment, the recombinant bacteriophage comprises a genome encoding at least 5 heterologous antigen proteins, normally found in two different organisms. In an embodiment, the recombinant bacteriophage comprises a genome encoding at least 3 heterologous antigen proteins, normally found in a three different organisms. In an embodiment, the recombinant bacteriophage comprises a genome encoding at least 4 heterologous antigen proteins, normally found in three different organisms. In an embodiment, the recombinant bacteriophage comprises a genome encoding at least 5 heterologous antigen proteins, normally found in three different organisms.

In an embodiment, the recombinant bacteriophage is incapable of carrying out the lysogenic cycle. This may be achieved by deleting portions of the phage genome polynucleotide that encode enzymes required for the lysogenic cycle, for example genes encoding recombinases. Such portions of polynucleotide are optionally replaced by a gene encoding a heterologous protein. In an embodiment, such portions of polynucleotide are replaced by a gene encoding a killing gene, for example a SASP gene or a CRISPR-Cas nuclease (Mehta K et al Biotechnology and Bioenginerring (2016) 113; 2568-2576), WO 04/113375, WO 16/55585, WO 16/55584, WO 16/55586, WO 16/55587).

In an embodiment, the recombinant bacteriophage is capable of entering a pathogenic bacterium such as staphylococcal, streptococcal Shigella, Pseudomonas, Propionibacterium, Acinetobacter, E. coli, P. aeruginosa, C. difficile, P. acnes, K. pneumoniae, N. meningitidis, or N. gonorrhaea bacterium. The recombinant bacteriophage contains a phage genome polynucleotide which optionally comprises a gene encoding a protein which specifically binds to one of the above mentioned bacteria. Such genes are optionally retained in the phage genome polynucleotide. In an embodiment, the recombinant bacteriophage is adapted to enter a S. aureus bacterium.

In an embodiment, the recombinant bacteriophage is adapted to degrade biofilm. In an embodiment this is achieved by engineering the phage to express biofilm disruptive enzymes. In an embodiment, the recombinant bacteriophage genome polynucleotide contains a gene encoding dispersin B (DspB) (Itoh Y et al (2005) J. Bacteriol. 187: 382-387), a gene encoding a depolymerase carried on the surface of phage which degrades bacterial capsular polysaccharides (Hughes K A et al Microbiology 144: 3039-3047 (1998))

In an embodiment, the heterologous gene encodes a staphylococcal protein selected from the group consisting of SitC/MntC/saliva binding protein, EbhA, EbhB, Elastin binding protein (EbpS), EFB (FIB), SBI, ClfA, SdrC, SdrG, SdrH, Lipase GehD, SasA, FnbA, FnbB, Cna, ClfB, FbpA, Npase, IsaA/PisA, SsaA, EPB, SSP-1, SSP-2, HBP, Vitronectin binding protein, fibrinogen binding protein, coagulase, Fig and MAP, IsdA, IsdB, HarA, MntC, alpha toxin (Hla), detoxified alpha toxin point mutation, optionally with a point mutation at H35, RNA III activating protein (RAP), protein A, a variant of protein A. In an embodiment, the heterologous gene encodes a protein described in WO 06/32472.

In an embodiment, the recombinant bacteriophage comprises genes encoding a heterologous antigen protein. When the recombinant bacteriophage enters a bacterial host cell, expression of the heterologous antigen protein is driven by an appropriate promoter allowing the heterologous antigen protein to be released from the bacterial host cell, allowing the immune system of a mammalian host to generate an immune response against the heterologous antigen protein. The immune response may generate antibodies against the heterologous antigen protein (humoral response) or may generate a T-cell mediate immune response (cellular response) or the immune response may be a mix of humoral and cellular components.

In an embodiment, the recombinant bacteriophage comprises a phage genome polynucleotide including a gene encoding a heterologous antigen protein which is under the control of a strong promoter and a killing gene encoding a protein that is capable of killing a host bacterium under the control of a weak and/or late promoter, optionally wherein the phage genome polynucleotide is engineered such that the gene encoding a heterologous antigen protein replaces a phage gene encoding a structural protein and the killing gene replaces a gene involved in the lysogenic cycle. This allows the recombinant bacteriophage to be incapable of producing viable progeny phage and incapable of carrying out a lysogenic cycle. However, the recombinant bacteriophage is capable of generating a heterologous antigen protein in a quantity sufficient to prime an immune response and to kill the bacterial host through the production of a protein capable of killing the host bacterium.

In an embodiment, the recombinant bacteriophage comprises a phage genome polynucleotide including a gene encoding a heterologous antigen protein which is under the control of a strong promoter and a killing gene encoding a protein that is capable of killing a host bacterium under the control of a weak and/or late promoter, optionally wherein the phage genome polynucleotide is engineered such that the gene encoding a heterologous antigen protein replaces a phage gene encoding a structural protein and the killing gene replaces a gene involved in the lysogenic cycle. This allows the recombinant bacteriophage to be incapable of producing viable progeny phage and incapable of carrying out a lysogenic cycle. However, the recombinant bacteriophage is capable of generating a heterologous antigen protein in a quantity sufficient to prime an immune response and to kill the bacterial host through the production of a protein capable of killing the host bacterium. In addition the recombinant bacteriophage is adapted to bind to a host bacterium through containing a modified component (for example a tail fibre or plate) which is engineered to bind to the required host bacterium with higher affinity than the equivalent component of a wild type bacteriophage.

In an embodiment, the recombinant bacteriophage comprises a phage genome polynucleotide including a gene encoding a heterologous antigen protein which is under the control of a strong promoter and a killing gene encoding a protein that is capable of killing a host bacterium under the control of a weak and/or late promoter, optionally wherein the phage genome polynucleotide is engineered such that the gene encoding a heterologous antigen protein replaces a phage gene encoding a structural protein and the killing gene replaces a gene involved in the lysogenic cycle. This allows the recombinant bacteriophage to be incapable of producing viable progeny phage and incapable of carrying out a lysogenic cycle. However, the recombinant bacteriophage is capable of generating a heterologous antigen protein in a quantity sufficient to prime an immune response and to kill the bacterial host through the production of a protein capable of killing the host bacterium. In addition the recombinant bacteriophage is adapted to degrade biofilm (for example by containing a gene under the control of a promoter that expresses biofilm disruptive enzymes) and is adapted to bind to a host bacterium through containing a modified component (for example a tail fibre or plate) which is engineered to bind to the required host bacterium with higher affinity than the equivalent component of a wild type bacteriophage.

A further aspect of the invention is a recombinant bacteriophage genome polynucleotide which is optionally contained within the bacteriophage of the invention or is freestanding. The invention encompasses the recombinant bacteriophage genome polynucleotide associated with any of the recombinant bacteriophage described above. In an embodiment, the recombinant bacteriophage genome polynucleotide comprises a heterologous antigen gene encoding a heterologous antigen protein, wherein the antigen gene does not encode a fusion protein of a phage capsid protein and a heterologous protein.

In a further embodiment, the recombinant bacteriophage genome polynucleotide comprises a heterologous antigen gene encoding a heterologous antigen protein and a killing gene encoding a protein that is capable of killing a host bacterium.

In an embodiment, the recombinant bacteriophage genome polynucleotide retains a sequence associated with the packaging of the genome into a phage capsid and retains genes associated with transcription and/or replication of the bacteriophage genome but does not retain all the genes required for making all structural elements of a complete bacteriophage. Some genes encoding structural proteins of a bacteriophage are optionally replaced with genes encoding one or more heterologous antigens, as described above. In an embodiment, at least one gene encoding a structural protein of the bacteriophage is/are replaced by at least one gene encoding a protein that is capable of killing a host bacterium. In an embodiment at least one gene encoding a structural protein of the bacteriophage is/are replaced by at least one gene encoding a heterologous antigen protein and at least one gene encoding a protein that is capable of killing a host bacterium.

In an embodiment, the at least one gene encoding a heterologous antigen protein is under the control of a strong promoter and/or an early promoter. In an embodiment, the at least one gene encoding a protein that is capable of killing the host bacterium is under the control of a weak promoter or a late promoter.

A further embodiment of the invention is a pharmaceutical compostion comprising the recombinant bacteriophage or the recombinant bacteriophage genome polynucleotide described above. In an embodiment, the pharmaceutical composition further comprises a pharmaceutically acceptable excipient, for example excipients to allow administration as a topical cream or ointment.

A further aspect of the invention is a vaccine comprising the recombinant bacteriophage or the recombinant bacteriophage genome polynucleotide of the invention.

A further aspect of the invention is medical uses and methods of treatment for the recombinant bacteriophage of the invention. Accordingly, there is provided a recombinant bacteriophage comprising a phage genome polynucleotide including a gene encoding a heterologous protein, wherein the heterologous protein is not expressed as part of a phage coat/capsid protein, for use in the prophylactic prevention of infectious disease. The infectious disease optionally comprises a bacterial, viral or fungal infection, for example a *Staphylococcus aureus* infection.

Similarly there is provided a method of treatment comprising the steps of: a) administering a recombinant bacteriophage comprising a phage genome polynucleotide including a gene encoding a heterologous protein, to a patient in need thereof such that the recombinant bacteriophage contacts a bacterium; b) entry of the bacteriophage genome polynucleotide into the bacterium, and expression of the heterologous antigen protein at a sufficient level for an immune response to be elicited against the heterologous protein.

The primary use of the recombinant bacteriophage of the invention is for the treatment and/or prevention of disease, particularly infectious disease involving bacterial infection or diease involving bacterial and viral or bacterial and fungal components. The recombinant bacteriophage of the invention expresses at least one heterologous antigen at a level sufficient for an immune response to be elicited against the heterologous antigen. The recombinant bacteriophage also expresses a killing gene so that the bacterial host is killed following the expression of the antigen. In this way, a infection is treated by killing a bacterial component of the infection and an immune response is primed.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1 Production of an Recombinant Bacteriophage

To effectively produce the engineered bacteriophage the bacteriophage genome is inserted into a yeast artificial chromosome (YAC) or bacterial artificial chromosome (BAC) backbone that includes components for selection and replication in yeast or bacteria, respectively.

Alternatively, the phage genome can be engineered directly within the bacteria by using a recombineering competent bacteria (FIG. 1). For example as described in Nobrega F L. et al. Trends in Microbiology 2015 23:185

Figure 2:
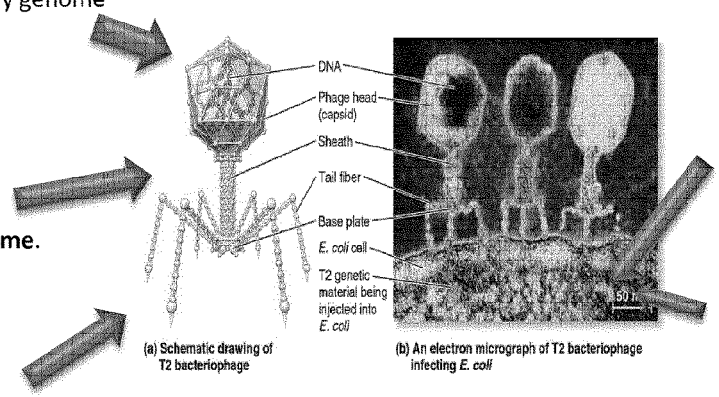

There are many possibilities for the genetic engineering of phage are shown in FIG. 2 Portions of the bacteriophage genome can be deleted to obtain a minimum synthetic bacteriophage genome which retains the the sequences essential for transcription and translation and the packaging signal. Other gene including those enoding proteins involved in the lysogenic cycle and capsid proteins can be deleted and replaced with selected genes. The four possibilities disclosed in FIG. 2 include i) the killer gene (under the control of a weak or late promoter) which encodes a protein capable of killing the selected host cell, ii) at least one heterologous antigen gene, under the control of a strong or early promoter to allow high enough levels of expression before the host bacterium is killed, iii) a modified tail fibre/plate to allow the bacteriophage to infect the required range of bacterial host cells and iv) optionally a gene encoding a biofilm destroping enzyme. The selective removal and replacement of genes allows the bacteriophage genome to retain approximately the same size.

Figure 3:
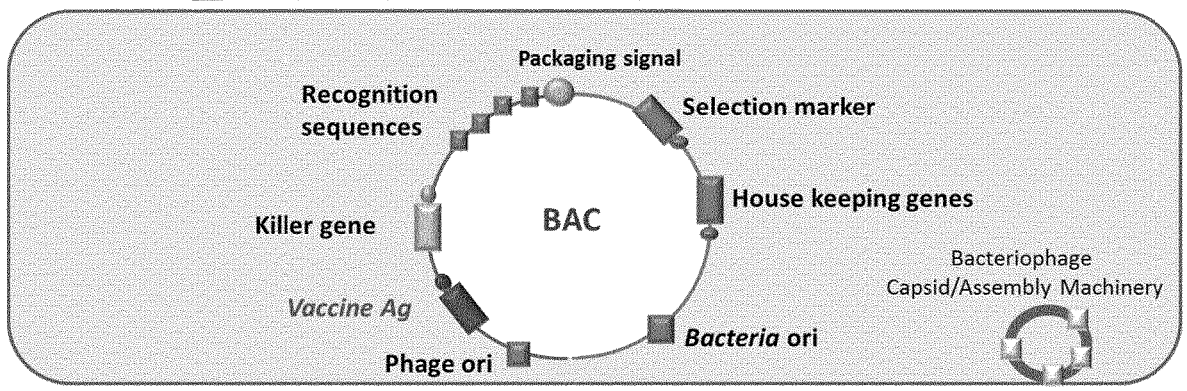
FIG. 3—demonstrates the intended use of recombinant bacteriophages of the invention.
Figure 3:
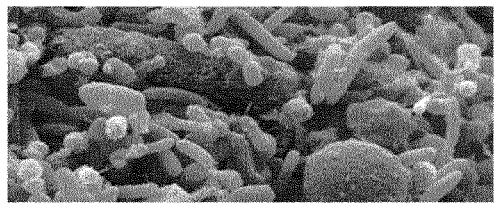

The engineered bacteriophage is based on a minimum phage genome that includes essential phage genome components such as origin of replication (ori), packaging signal(s) and phage tail recognition components in addition to several heterologous components. The first of these components is at least one gene that encodes a vaccine antigen driven by a early or strong promoter. The second component is a gene encoding a killer molecule, whose expression is driven by a late or weak promoter. A third optional component is at least one gene encoding a depolymerase which is capable of destroying biofilms, whose expression is driven by a late promoter. The engineered bacteriophage is missing some essential genes so will not be able to initiate a full lytic or lysogenic cycle when used in the treatment of a mammalian subject. However, it will be able to replicate in *E. coli* or other non-pathogenic bacterial cells which contain to bacteriophage capsid assembly machinery, as shown in FIG. 3. For example a BAC construct includes both the engineered bacteriophage components and the bacteria specific components (see FIG. 3).

Phage Amplification and Purification

The engineered bacteriophage is produced in either *E. coli*. or a non-pathogenic strain of the bacterial target that expresses the bacteriophage capsid machinery under an inducible or a constitutive promoter.

The bacterial host cell is transfected with a bacterial artificial genome (BAC) construct or appropriate artificial engineered bacteriophage genome. As the bacterial host cell expresses the capsid machinery in trans, the bacterial host cell is capable of producing phage in which the genome of the engineered bacteriophage is packaged into complete bacteriophage. The transfected bacterial host cell is cultured in a suitable medium, allowing phage replication to proceed in the bacterial host cells. The phage growth can be monitored using culture turbidity, pO2, pH, or may be allowed to continue for a pre-determined length of incubation time. Based on known phage life cycle parameters. Infected cells, concentrated by centrifugation, may be treated with organic solvents (e.g. chloroform), EDTA, lysozyme or bacteriophage lysins to induce lysis and release the phage. (Gill J J and Hyman P Current Pharmaceutical Biotechnology 2010 11:2-14).

After lysis, remaining cells or larger cell debris are removed by low-speed centrifugation and the phage containing supernatant is retained. The phage can then be purified by precipitation with polyethylene glycol (PEG) followed by removal of PEG by dialysis (Yamamoto et al (1970) 40; 734-744) or by passing through a 0.2 mm filter to remove cell debris and then using tangential flow filtration against a 100 kDa membrane which retains phage but allows passage of media components and some cellular proteins. This step is followed by scalable chromatography that can yield a recovery rate of up to 70% (Yamamoto et al (1970) 40; 734-744). Hydroxyapatite chromatography of phage display virions is described in Biotechniques (2005) 39; 879. T4 bacteriophage can be purified by using strong anion exchange monolithic chromatography columns (Smrekar F et al J. Chromotogr. B Analyt. Technol. Life. Sci. (2008) 861; 177-180).

Treatment of Disease Using Bacteriophage Adapted to Prime & Kill

The overall goal of the therapeutic treatment with engineered bacteriophage is to treat acute or chronic bacterial disease and prevent disease relapse long term via persistent immunity.

Both in vitro & in vivo experiments are done to demonstrate that the bacteriophage prime and kill concept is capable of killing the host bacteria bacteria whilst allowing sufficient vaccine antigen to be produced to lead to the priming of an immune response against the chosen antigen. For in vitro demonstration the engineered bacteriophage will infect the bacteria. The vaccine antigen is expressed under the control of a strong promoter so that sufficient antigen is produced before the host cell is killed. The antigen may be either secreted whilst the host bacterium is alive or released from the bacterial cytoplasm after the bacterium is killed. A killer molecule is expressed under the control of a late promoter so that the killer molecule is not expressed until sizeable amounts of the priming antigen have been expressed. When a sufficient level of the killer molecule has been expressed, this will kill the bacteria. These experiments therefore aim to demonstrate both killing efficacy and the potential to induce durable immunity.

An in vivo preclinical model using a bacteria as a pathogen is used to demonstrate the 'Prime & Kill" concept. Animals are infected with the bacterial pathogen in an established infection model. The animals are subsequently treated with the engineered bacteriophage. Blood sample are taken from the animals after 7-14 days so that immune responses against the vaccine antigen can be assessed and The ability of the bacteriophage to kill the bacterial pathogen is demonstrated by assessing the number of CFUs of the bacterium isolatable from animals treated with bacteriophage compared to a control group treated with excipient. The induction of a protective immune response directed to the vaccine antigen is monitored by a suitable assay such as an ELISA on serum taken from the animal.

Subsequent experiments demonstrate protection against the recurrence of disease caused by the same bacteria. In these experiments animals are infected with the bacterial pathogen and subsequently with the engineered bacteriophage. An intial cycle of Prime & Kill takes place in which the bacteriophage infected bacteria prime an immune response and are subsequently killed by the killer molecule expressed by the recombinant bacteriophage. The initial cycle of Prime & Kill allows the animals to survive the initial infection with the bacterial pathogen and become primed. At a later time point, the primed animals are challenged with the pathogen against which they have been primed. The survival, recovery and pathogen load of the primed animals will be compared to that of a control group of animals.

To enhance the capacity of bacteriophage concept efficacy we also consider the option of including biofilm degrading depolymerase in the engineered bacteriophage construct. The challenge experiments described above are repeated using either a bacteriophage engineered to express a vaccine antigen and a killer molecule or a bacteriophage engineered to express a vaccine antigen, a killer molecule and a depolymerase, capable of degrading biofilm. The ability of the depolymerase to enhance the efficacy of the engineered bacteriophage is demonstrated.

Example 2—Demonstration of Effectiveness of a Prime and Kill Bacteriophage

Both in vitro & in vivo experiments are done to demonstrate that engineered bacteriophage infect bacteria, express the vaccine antigen and then kill the bacteria. Two different preclinical challenge models are used to demonstrate the capacity of the engineered bacteriophage to kill the pathogen, induce an immune response & protect against recurrent infection.

*Staphylococcus aureus* is used as the the model pathogen to demonstrate the concept. The *Staphylococcus aureus* alpha toxin vaccine antigen is selected for the preclinical proof of concept.

A bacteriophage genome is engineered in a BAC (or appropriate artificial engineered bacteriophage genome) such that it contains a tagged, detoxified α-toxoid from *S. aureus* under the control of a strong early promoter, as the vaccine antigen and the usual lytic machinery of the bacteriophage under a late promoter as the killer molecule. Other components of the bacteriophage genome are deleted so that the bacterphage genome would not produce viable bacteriophage without the help of a host cell that contains bacteriophage capsid machinery. The BAC is transfected into *E. coli* that expresses the bacteriophage capsid machinery under an inducible or a constitutive promoter and cultured so that bacteriophage are produced. These are harvested and purified as described above.

The purified engineered bacteriophage are assessed in vitro for their ability to kill (*S. aureus*) a heterologous host bacterium which the bacteriophage is engineered to infect. In a second in vitro assay, the expression of a tagged alpha toxoid in host bacteria (*S. aureus*) infected by the engineered bacteriophage is assessed by Western blot using antibodies specific for the tagged alpha toxoid.

After demonstrating that the engineered bacteriophage both efficiently kills and expresses alpha toxoid, the engineered bacteriophage is assessed in two in vivo models: a mouse intranasal lethal challenge model and a guinea pig dermonecrosis model. The mouse intranasal lethal challenge model involves challenging C57 black mice with $10^7$-$10^9$ CFU of a S. aureus strain such as Newman or Wright. The ability of the engineered bacteriophage to provide protection and to generate an immune response is assessed by treating with the engineered bacteriophage shortly after bacterial challenge. Survival is monitored for seven days and the immune response is assessed after 7-21 days. For the guinea pig dermonecrosis model, giunea pigs are challenged intradermally at six sites per guinea pig using a alpha toxin secreting strain of S. aureus (for example Newman or Wright). The ability of the engineered bacteriophage to provide protection and to generate an immune response is assessed by treating with the engineered bacteriophage shortly after bacterial challenge. Survival is monitored for seven days and the immune response is assessed after 7-21 days.

The invention claimed is:

1. A recombinant bacteriophage comprising
a phage genome polynucleotide including a deletion of at least one gene encoding a bacteriophage structural protein;
a gene encoding a heterologous antigen protein(s) without an appropriate leader sequence, wherein the expression of the heterologous antigen protein is driven by a strong promoter, and
a killing gene encoding a protein that kills a host bacterium, wherein the expression of the killer gene is driven by a weak promoter,
wherein the recombinant bacteriophage is incapable of carrying out a lysogenic cycle by deletion of a portion of the phage genome polynucleotide that encodes an enzyme required for the lysogenic cycle,
wherein the recombinant bacteriophage is adapted to bind to a host bacterium and insert the phage genome polynucleotide into said host bacterium;
wherein following entry of the recombinant bacteriophage into a host bacterium, expression of the heterologous antigen protein is driven by the strong promoter,
wherein the heterologous antigen is released from the host bacterium and the heterologous antigen protein(s) is not expressed as part of a phage coat/capsid protein;
wherein the heterologous antigen protein, after expression is released into the cytoplasm of a bacterium infected by the bacteriophage due to the absence of the appropriate leader sequence.

2. The recombinant bacteriophage of claim 1, wherein the host bacterium is E. coli.

3. The recombinant bacteriophage of claim 1, wherein the bacteriophage is Myoviridae.

4. The recombinant bacteriophage of claim 1, wherein the heterologous antigen protein is a bacterial protein originating from a Gram positive bacterium.

5. The recombinant bacteriophage of claim 1, wherein the heterologous antigen protein is a protein from E. Coli.

6. The recombinant bacteriophage of claim 5, wherein the heterologous antigen protein, after expression, is directed to the surface of a bacterium infected by the bacteriophage.

* * * * *